(12) United States Patent
Vadlamudi-Reddy et al.

(10) Patent No.: US 12,016,670 B2
(45) Date of Patent: Jun. 25, 2024

(54) MULTIPLE THRESHOLD CHECKERS FOR SPECIFIC APPLICATIONS AND FFT BASED BREATHING DETECTION FOR PRESENCE

(71) Applicants: STMicroelectronics (Grenoble 2) SAS, Grenoble (FR); STMicroelectronics, Inc., Coppell, TX (US)

(72) Inventors: Kalyan-Kumar Vadlamudi-Reddy, San Jose, CA (US); Darin K Winterton, San Jose, CA (US); Pierre-Loic Felter, Grenoble (FR); Olivier Lemarchand, Grenoble (FR)

(73) Assignees: STMICROELECTRONICS (GRENOBLE 2) SAS, Grenoble (FR); STMICROELECTRONICS, INC., Coppell, TX (US)

( * ) Notice: Subject to any disclaimer, the term of this patent is extended or adjusted under 35 U.S.C. 154(b) by 632 days.

(21) Appl. No.: 16/832,515

(22) Filed: Mar. 27, 2020

(65) Prior Publication Data
US 2021/0298637 A1  Sep. 30, 2021

(51) Int. Cl.
*A61B 5/08* (2006.01)
*G06F 17/14* (2006.01)

(52) U.S. Cl.
CPC ............ *A61B 5/0803* (2013.01); *A61B 5/082* (2013.01); *G06F 17/142* (2013.01)

(58) Field of Classification Search
None
See application file for complete search history.

(56) References Cited

U.S. PATENT DOCUMENTS

| | | | |
|---|---|---|---|
| 1,557,965 A | 10/1925 | Beaumont | |
| 4,283,989 A * | 8/1981 | Toulios | F41A 21/32 342/60 |
| 5,319,611 A | 6/1994 | Korba | |
| 5,686,896 A | 11/1997 | Bergman | |
| 5,748,295 A * | 5/1998 | Farmer | G01S 17/58 356/28.5 |
| 6,697,723 B2 | 2/2004 | Olsen et al. | |
| 7,019,641 B1 | 3/2006 | Lakshmanan et al. | |
| 7,403,269 B2 | 7/2008 | Yamashita et al. | |
| 8,428,275 B2 | 4/2013 | Yoshida et al. | |

(Continued)

FOREIGN PATENT DOCUMENTS

| | | |
|---|---|---|
| EP | 3375362 A1 * | 9/2018 |
| WO | 9834206 A1 | 8/1998 |

(Continued)

OTHER PUBLICATIONS

Kim, B., et al., "A Low-Complexity FMCW Surveillance Radar Algorithm Using Two Random Beat Signals", MDPI, sensors, Jan. 2019, 17 Pages.

*Primary Examiner* — Yi-Shan Yang
*Assistant Examiner* — Samuel C Kim
(74) *Attorney, Agent, or Firm* — Slater Matsil, LLP

(57) ABSTRACT

In accordance with embodiments, methods and systems for utilizing multiple threshold checkers are provided. A range sensor collects measurement data. The range sensor examines the measurement data based on multiple threshold checkers to determine satisfaction of a trigger condition. In response to the satisfaction of the trigger condition, the range sensor provides the measurement data to a host computing device of the range sensor.

20 Claims, 12 Drawing Sheets

(56) References Cited

U.S. PATENT DOCUMENTS

| | | |
|---|---|---|
| 8,454,528 B2 | 6/2013 | Yuen et al. |
| 8,560,128 B2 | 10/2013 | Ruff et al. |
| 9,158,904 B1 | 10/2015 | Ross et al. |
| 10,052,048 B2 | 8/2018 | Klewer et al. |
| 10,293,239 B2 | 5/2019 | Balakrishnan et al. |
| 11,209,890 B2 | 12/2021 | Azam et al. |
| 11,314,306 B2 | 4/2022 | Kosugi |
| 2007/0013509 A1 | 1/2007 | Lakshmanan et al. |
| 2010/0130873 A1* | 5/2010 | Yuen .................... A61B 5/1126 600/595 |
| 2010/0163713 A1* | 7/2010 | Cheng .................... G06F 1/3265 250/214 AL |
| 2011/0010572 A1 | 1/2011 | Chen |
| 2011/0296163 A1* | 12/2011 | Abernethy ............ G06F 1/3203 713/100 |
| 2013/0214166 A1 | 8/2013 | Barlow et al. |
| 2015/0154849 A1* | 6/2015 | Matsui .................... G01S 17/04 342/28 |
| 2015/0161434 A1* | 6/2015 | Ross ........................ G06F 21/32 382/118 |
| 2017/0051481 A1 | 2/2017 | Mercer |
| 2017/0215772 A1* | 8/2017 | Garn .................... A61B 5/0806 |
| 2017/0357788 A1 | 12/2017 | Ledvina et al. |
| 2018/0157376 A1 | 6/2018 | Lemarchand ............ G01V 8/12 |
| 2019/0209046 A1* | 7/2019 | Addison .............. A61B 5/0077 |
| 2019/0246172 A1 | 8/2019 | Cheong et al. |
| 2021/0109486 A1 | 4/2021 | Hamlin et al. |

FOREIGN PATENT DOCUMENTS

| | | |
|---|---|---|
| WO | 2011132118 A2 | 10/2011 |
| WO | 2012002904 A1 | 1/2012 |

\* cited by examiner

| Dataready FLAG (GLOBAL FLAG) | NoTarget FLAG (INDIVIDUAL CHECKER FLAG) | | CHECKER PER TARGET | | | | CHECKER PER ZONE | | |
|---|---|---|---|---|---|---|---|---|---|
| | | | A (TARGET FOUND) | B (TARGET FOUND) | C (TARGET FOUND) | NO TARGET FOUND | A | B | C |
| 0 | 0 | InWindow | 0 | 1 | 0 | 0 | 0 | 1 | 0 |
| | | OutOfWindow | 1 | 0 | 1 | 0 | 1 | 0 | 1 |
| | | Less than low | 1 | 0 | 0 | 0 | 1 | 0 | 0 |
| | | Higher than high | 0 | 1 | 1 | 0 | 0 | 1 | 1 |
| | 1 | InWindow | 0 | 0 | 0 | 1 | 0 | 0 | 0 |
| | | OutOfWindow | 1 | 0 | 0 | 1 | 1 | 0 | 1 |
| | | Less than low | 1 | 0 | 0 | 1 | 0 | 0 | 0 |
| | | Higher than high | 0 | 1 | 1 | 1 | 1 | 1 | 1 |
| 1 | 0 | InWindow | 1 | 1 | 1 | 1 | 1 | 1 | 1 |
| | | OutOfWindow | 1 | 1 | 1 | 1 | 1 | 1 | 1 |
| | | Less than low | 1 | 1 | 1 | 1 | 1 | 1 | 1 |
| | | Higher than high | 1 | 1 | 1 | 1 | 1 | 1 | 1 |
| | 1 | InWindow | 1 | 1 | 1 | 1 | 1 | 1 | 1 |
| | | OutOfWindow | 1 | 1 | 1 | 1 | 1 | 1 | 1 |
| | | Less than low | 1 | 1 | 1 | 1 | 1 | 1 | 1 |
| | | Higher than high | 1 | 1 | 1 | 1 | 1 | 1 | 1 |

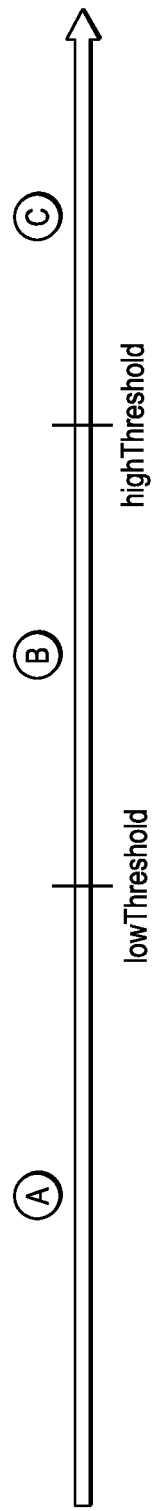

Ⓐ    Ⓑ    Ⓒ
lowThreshold    highThreshold

FIG. 3

| CHECKER | checker_param low_thresh | checker_param high_thresh | checker_param type | checker_type | ZONE NUMBER | OPTIONAL checker_type |
|---|---|---|---|---|---|---|
| 0 | 1050mm | 1550mm | MEDIAN_RANGE_MM | IN_WINDOW | 0 | NO TARGET DETECTED, OR |
| 1 | 350mm | 0 (NA) | MEDIAN_RANGE_MM | LESS_THAN_EQUAL MIN_CHECK | 1 | OR |
| 2 | 50.0kcps/SPAD | 500kcps/SPAD | PEAK_RATE_KCPS_PER_SPAD | IN_WINDOW | 0 | AND |
| 3 | 0 (NA) | -20C | SENSOR_TEMP | GREATER_THAN MAX_CHECKER | 0 | AND |
| 4 (LAST CHECKER) | 50kcps/SPAD | 0 (NA) | AMB_RATE_KCPS_PER_SPAD | LESS_THAN_EQUAL MIN_CHECKER | 1 | AND |

FIG. 4A

| CHECKER | checker_param low_thresh HEX (DECIMAL) | checker_param high_thresh HEX (DECIMAL) | checker_param type HEX (DECIMAL) | checker_type HEX (DECIMAL) | ZONE NUMBER HEX (DECIMAL) | OPTIONAL checker_type HEX (DECIMAL) |
|---|---|---|---|---|---|---|
| 0 | 0x0000 1068 (4200) | 0x0000 1838 (6200) | 0x01 (1) | 0x00 (0) | 0x00 (0) | 0x01 (1) |
| 1 | 0x0000 0578 (1400) | 0x0000 0000 (0) | 0x01 (1) | 0x02 (2) | 0x01 (1) | 0x00 (0) |
| 2 | 0x0001 9000 (102,400) | 0x000F A000 (1,024,000) | 0x02 (2) | 0x00 (0) | 0x00 (0) | 0x02 (2) |
| 3 | 0xFFFF FFEC (-20) | 0x0B (11) | 0x03 (3) | 0x00 (0) | 0x02 (2) |
| 4 (LAST CHECKER) | 0x0000 0000 (0) | 0x0000 1900 (6400) | 0 (NA) | 0x08 (8) | 0x02 (2) | (0x81) 129 (NOTE, BIT 7 SET TO 1 FOR LAST CHECKER) | 0x02 (2) |

FIG. 4B

| PURPOSE | API | ARGUMENTS | RETURN |
|---|---|---|---|
| SET INTERRUPT CONTROL GLOBAL AND VALID TARGET STATUS LIST CONFIG | sttof_al_set_ic_global_cfg | 1. struct sttof_device_handle_t *ptr<br>2. struct dci_ic_grp_global_cfg_t *ptr<br>3. struct dci_ic_grp_valid_target_cfg_t *ptr | SUCCESS/FAILURE |
| SET CHECKERS | sstof_al_set_ic_checkers | 1. struct sttof_device_handle_t *ptr<br>2. struct dci_ic_grp_checkers_t *ptr | SUCCESS/FAILURE |
| GET INTERRUPT STATUS FOR EACH ZONE | sttof_al_get_ic_op_status | 1. struct sttof_device_handle_t *ptr<br>2. struct dci_ic_grp_op_status_t *ptr | 1. SUCCESS/FAILURE<br>2. struct dci_ic_grp_op_st *ptr |

FIG. 5A

```
struct dci_ic_grp__global_cfg_t        ic_grp__global_cfg;
struct dci_ic_grp__valid_target_cfg_t   ic_grp_valid_target_cfg;

//Initialize valid status list
for (int i = 0;  i < 8; i++)
{
        ic_grp_valid_target_cfg.valid_target_status[i] = 5;
}

/* Initialize Global config */
ic_grp__global_cfg.polarity              = 0; //Not used currently in the FW
ic_grp__global_cfg.thresholds_enable     = 1; //Enable interrupt controls
ic_grp__global_cfg.extra_cfg_enable      = 0; //Not used currently in FW
ic_grp__global_cfg.check_any_target      = 1; //Not used currently in FW /* Configure the FW */
status = sttof_al_set_ic_global_cfg(&L5Dev,
                                    &ic_grp__global_cfg,
                                    &ic_grp_valid_target_cfg);
if (status < STATUS_OK)      {
   uart_printf("Error at %s (%d) : %d\n", __func__, __LINE__, status) ;
}
return status;
```

FIG. 5B

```
struct dci_ic_grp__checkers_t        ic_grp_checkers;
struct dci_ic_grp__checker_cfg_t *checker_cfgs_ptr;
uint8_t checker_type         = IN_WINDOW;           // Check if target is in window
uint8_t checker_param_type   = MEDIAN_RANGE_MM;     // Check for Range value
int32_t low_threshold        = 200 << 2;            // 200mm
int32_t high_threshold       = 400 << 2;            // 400mm // Set individual checkers
checker_cfgs_ptr = &(ic_grp__checkers.dci_ic_checker_0);
// Clear memory to zero
memset (&ic_grp__checkers, 0, sizeof (struct dci_ic_grp__checkers_t));
for    (i = 0, i < 16; i++)       {
        checker_cfgs_ptr[i]. checker_param_type = checker_param_type;
        checker_cfgs_ptr[i]. checker_param_low_thresh = low_threshold;
        checker_cfgs_ptr[i]. checker_param_high_thresh = high_threshold;
        checker_cfgs_ptr[i]. checker_type = checker_type;
        checker_cfgs_ptr[i]. zone_num = i;
        checker_cfgs_ptr[i]. optional_checker_type = 0;
        if (i == 15) {// Add 0x80 to set MSB -> this is the last zone
                checker_cfgs_ptr [i]. zone_num += 0x80;
        }
}
status = sttof_al_set_ic_checkers (&L5Dev, &ic_grp__checkers);
if (status < STATUS_OK)       {
   uart_printf("Error at %s (%d) : %d\n", __func__, __LINE__, status) ;
}
return status;
```

FIG. 5C

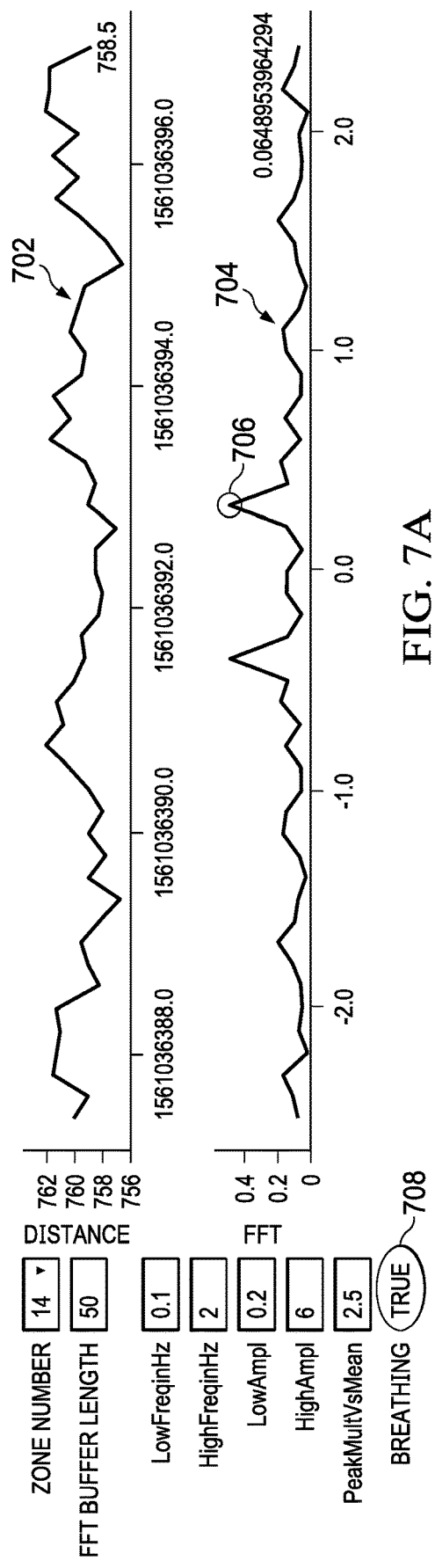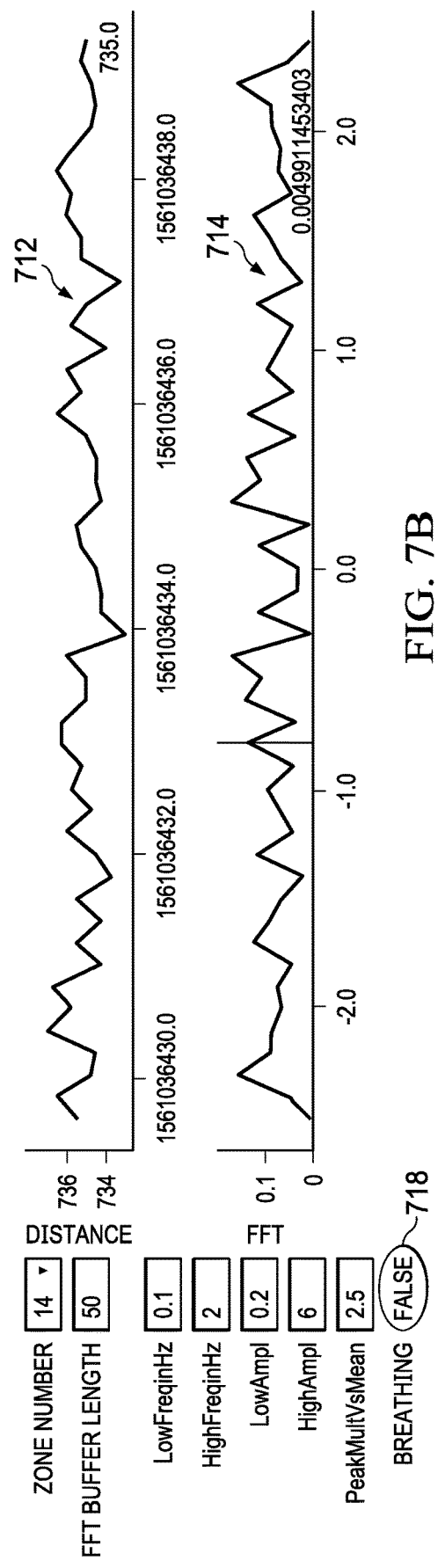
FIG. 7A
FIG. 7B

MULTIPLE THRESHOLD CHECKERS FOR SPECIFIC APPLICATIONS AND FFT BASED BREATHING DETECTION FOR PRESENCE

TECHNICAL FIELD

The present disclosure relates generally to systems and methods for processing of measurement data by a sensor, and, in particular embodiments, to processing of measurement data by a range sensor to determine presence.

BACKGROUND

A range sensor can be used to measure the distance of an object in front of the range sensor. A range sensor can be a single-zone range sensor or a multi-zone range sensor. Each zone corresponds to a different area detected by the range sensor. Examples of multi-zone range sensors include, but are not limited to, a 4-zone range sensor, a 16-zone range sensor, or a 64-zone range sensor.

A range sensor can work in conjunction with a host computing device, such as a laptop, to achieve a variety of features. For example, a range sensor may be integrated into a laptop and placed around the center position above the laptop's screen (e.g., right next to the camera of the laptop). Measurement data from the range sensor may be provided to the laptop for the laptop to determine presence information, such as the presence of a human user of the laptop.

Range sensors help maintain user privacy. In contrast to a laptop camera providing high resolution images of millions of pixels, measurement data from a range sensor is low resolution. For example, measurement data from a 16-zone range sensor contains 16 "pixels" of distance information, which hardly exposes any meaningful user privacy information. However, processing of a range sensor's measurement data has its own technical challenges.

Typically, a range sensor, such as a time of flight (ToF) sensor, has threshold detection based on distance only, where the range sensor would generate an output if a measured distance is within a certain range. One technical issue is that the range sensor can generate over 10K bytes of data (e.g., the distance per zone, the signal rate, the ambient rate, and the noise estimation, etc.) for a single range when using multiple zones. Further, the range detection can be performed at a rate of 60 per second. This is a huge amount of data for a host processor, such as the one on the host computing device, to handle, consuming a lot of power.

In conventional systems, external processing of the range sensor's measurement data is performed by the host processor of the host computing device. To process the measurement data, the host processor could not go to sleep because measurement data is continuously coming to the host processor from the range sensor to be analyzed. If a threshold checker based only on the distance is used, either false triggers could be raised (i.e., false positives) or events were not triggered when there should have been a trigger (i.e., false negatives).

Accordingly, technical improvement to technical problems of the conventional approach is desired to enhance efficiency and accuracy for processing the range sensor measurement data.

SUMMARY

In accordance with embodiments, methods and systems for utilizing multiple threshold checkers are provided. A range sensor collects measurement data. The range sensor examines the measurement data based on multiple threshold checkers to determine satisfaction of a trigger condition. In response to the satisfaction of the trigger condition, the range sensor provides the measurement data to a host computing device of the range sensor.

In some embodiments, to provide the measurement data to the host computing device, the range sensor may generate an interrupt signal to wake up the host computing device. The range sensor may receive, from the host computing device, a measurement data request. The range sensor may then send, to the host computing device, a measurement data response including the measure data.

In some embodiments, the multiple threshold checkers may comprise a first threshold checker and a second threshold checker. The first threshold checker may include a first data type and a first threshold range. The second threshold checker may include a second data type and a second threshold range. The first data type may be different from the second data type.

In some embodiments, the first data type may be one of a signal rate type, a reflectance type, a distance type, or an ambient rate type.

In some embodiments, the multiple threshold checkers may comprise a first subset of threshold checkers associated with a first zone measured by the range sensor. The multiple threshold checkers may further comprise a second subset of threshold checkers associated with a second zone measured by the range sensor.

In some embodiments, one device of the range sensor or the host computing device may perform breathing analysis operations using the measurement data. To perform the breathing analysis operations, the one device may perform fast Fourier transform (FFT) on the measurement data to generate transformed measurement data in the frequency domain. The one device may identify a highest peak in the transformed measurement data corresponding to breathing detection. The one device may confirm the breathing detection based on the identifying the highest peak.

In some embodiment, to identify the highest peak, the one device may determine that the amplitude of the highest peak is between a first amplitude threshold and a second amplitude threshold and that the amplitude is higher than N times of a mean of the transformed measurement data. N may be an integer great than or equal to 2.

In some embodiments, the measurement data may comprise first measurement data associated with a first zone and second measurement data associated with a second zone. To perform the FFT on the measurement data, the one device may determine that a first distance of the first measurement data is less than a zone selection distance threshold. The one device may determine that a second distance of the second measurement data is greater than the zone selection distance threshold. The one device may perform the FFT on the first measurement data without performing the FFT on the second measurement data.

In some embodiments, the range sensor may receive updated settings for at least one of the multiple threshold checkers. The updated settings may be based on a next event associated with a presence state machine running on the host computing device. The next event may be triggered by the providing the measurement data to the host computing device. The range sensor may examine the measurement data based on the multiple threshold checkers including the at least one threshold checker with the updated settings.

Sensor devices, computing devices, as well as computer program products, for performing the methods are also provided.

The foregoing has outlined rather broadly the features of an embodiment of the present disclosure in order that the detailed description of the disclosure that follows may be better understood. Additional features and advantages of embodiments of the disclosure will be described hereinafter, which form the subject of the claims of the disclosure. It should be appreciated by those skilled in the art that the conception and specific embodiments disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims

BRIEF DESCRIPTION OF THE DRAWINGS

For a more complete understanding of the present disclosure, and the advantages thereof, reference is now made to the following descriptions taken in conjunction with the accompanying drawings, in which:

FIG. 3 shows the truth table for a range sensor checker, according to some embodiments;

FIG. 4A shows an example of checker configurations for one zone, according to some embodiments;

FIG. 4B shows the example checker configurations for 5 checkers, according to some embodiments;

FIG. 5A shows the example application programming interface (API) definitions, according to some embodiments;

FIG. 5B shows the example code to configure the global configuration and the valid target status list, according to some embodiments;

FIG. 5C shows the example code to configure 16 checkers, according to some embodiments;

FIG. 7A shows the example signal patterns in the situation of human user breathing;

FIG. 7B shows the example signal patterns in the situation of a static chair;

Corresponding numerals and symbols in the different figures generally refer to corresponding parts unless otherwise indicated. The figures are drawn to clearly illustrate the relevant aspects of the embodiments and are not necessarily drawn to scale

DETAILED DESCRIPTION OF ILLUSTRATIVE EMBODIMENTS

The making and using of the presently preferred embodiments are discussed in detail below. It should be appreciated, however, that the present disclosure provides many applicable inventive concepts that can be embodied in a wide variety of specific contexts. The specific embodiments discussed are merely illustrative of specific ways to make and use the invention, and do not limit the scope of the invention.

Measurement data from range sensors can be processed for various purposes. One example is for presence detection. Techniques in this disclosure are mostly described in the context of presence detection as illustrative examples. The described techniques in this disclosure are not limited in the context of presence detection.

Figure 1A:
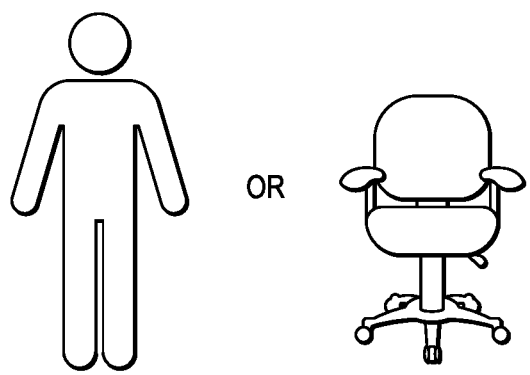
FIG. 1A shows example measurement data by a range sensor associated with 16 zones.

FIG. 1A depicts example measurement data by a range sensor associated with 16 zones. FIG. 1A shows that the range sensor measures distance data at a moment for 16 zones, such as the zones 102, 104, and 106. For examples, the measured distance data for the zones 104 and 106 are 822.25 millimeters (mm) and 405.00 mm, respectively. If there is no object or human user in front of the ranger sensor in the corresponding area of a zone, there may be no distance data measured. FIG. 1A shows that the zone 102 does not have distance data because there is no target (e.g., a static object or a human user) in front of the area corresponding to the zone 102.

Figure 1B:
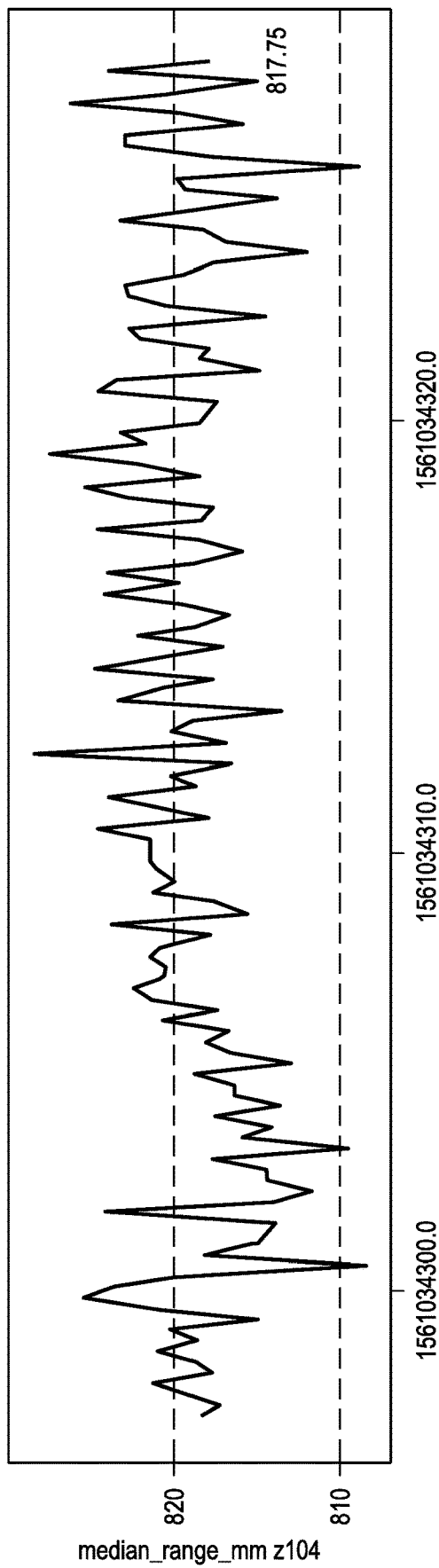
FIG. 1B shows example distance data for a zone measured by the range sensor in front of a stationary target (e.g., an object or a human) over time.

The range sensor may measure the distance data continuously over time. FIG. 1B shows the distance data measured by the range sensor in front of a stationary target (e.g., an object or a human) over time for a zone, such as the zone 104. A range sensor provides low resolution data (e.g., 4×4 for a 16-zone range sensor) to maintain user privacy. Further processing needs to be performed to determine what a static object or a human user is facing the sensor.

In conventional systems, a range sensor has threshold detection based on distance only. One technical challenge of the conventional systems is that a range sensor generates a huge amount of data to be processed by the processor of the host computing device (e.g., a laptop hosting the range sensor), consuming a lot of power.

Embodiments of this disclosure provides threshold checker techniques for pre-processing the data at the range sensor so that a specific application (e.g., a presence detection application) on the host computing device can look for certain details that the range sensor measures, and the range sensor only alerts the host computing device that an event has occurred if certain specific criteria are met. For a multi-zone range sensor, each zone can have specific checkers applied, and each zone can have different checkers. For example, for a presence detection application, the user can set up to 4 specific threshold checkers for checking that the signal rate, reflectance, distance, and ambient rates are all within specific ranges before an interrupt is triggered. One example interrupt is the trigger to wake up host processor on the host computing device.

By pre-analyzing more data in addition to the distance data against checker range values at the range sensor, the range sensor provides only data of interest to the specific application to the host processor for further analysis. In so doing, the embodiment techniques allow the host processor to go to sleep, which preserves power, while the range sensor keeps running and processing the measurement data internally. The range sensor may only wake up the host processor of the host computing device when an event occurs.

With the embodiment techniques, the range sensor performs more data analysis, which does not consume much more power because the range sensor is already running to collect the measurement data. In addition, because of the multiple threshold checkers, only a small portion of all the measurement data is sent to the host processor, and the overall power is actually conserved.

The embodiment techniques utilizing multiple threshold checkers may be used for a user presence detection application. The embodiments of the multiple threshold checkers are described in the context of the user presence detection for illustration purpose. The use of the multiple threshold checkers is not limited in the context of the user presence detection.

Figure 2A:
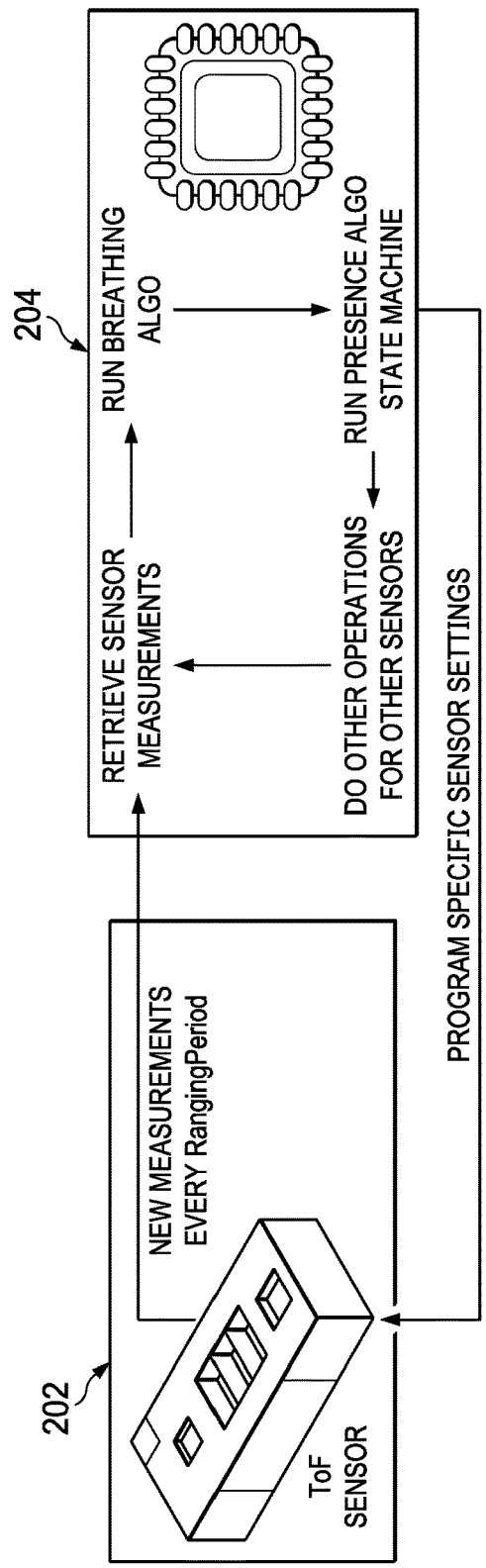
FIG. 2A illustrates the interaction between a range sensor and a host processor when the user is present, according to some embodiments.

FIG. 2A illustrates the interaction between a range sensor 202 and a host processor 204 when the human user is present, according to some embodiments. Both the range sensor 202 and the host processor 204 may be components of a host computing device. The host processor 202 may be a central processing unit (CPU) of the host computing device. The host processor 202 may also be a co-processor of the CPU of the host computing device. For example, the host processor 202 may be an Intel® integrated sensor hub (ISH). When a human user is detected, the range sensor 202 is continuously monitoring the scene and sends out the measurement data to the host processor for analysis. The range sensor 202 provides new measurement data for every ranging period, which is retrieved by the host processor 204. The host processor 204 may run breathing detection operations to detect the breathing pattern of the human user. The host processor 204 may then update the presence state machine. A new event may be triggered as the presence state machine is updated. As part of updating the presence state machine, the host processor 204 may program specific sensor settings (e.g., updating settings of the multiple threshold checkers). In some embodiments, the checker settings may be programmed when the human user absence has been detected. The host processor 204 may also perform other operations for other sensors, and continue to retrieve new measurement data from the range sensor 202 for the next ranging period.

Figure 2B:
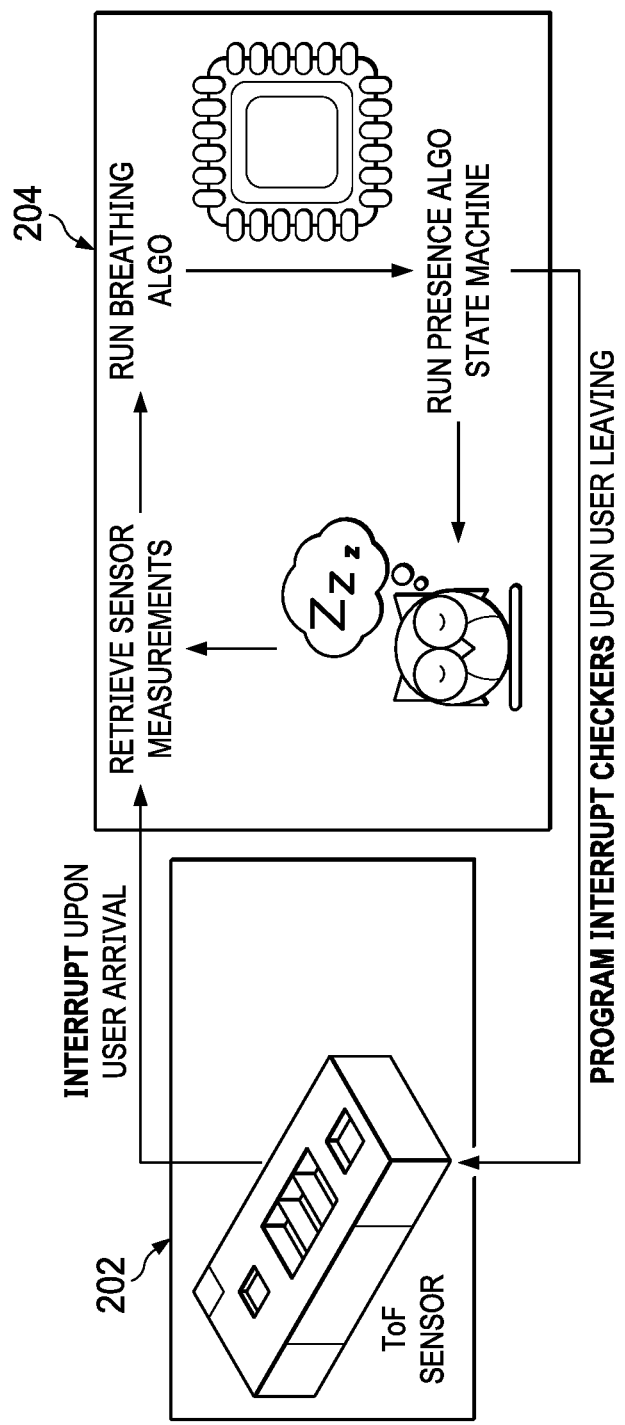
FIG. 2B illustrates the interaction between a range sensor and a host processor when the user is leaving, according to some embodiments.

FIG. 2B illustrates the interaction between the range sensor 202 and the host processor 204 when the human user is leaving, according to some embodiments. When the human user is leaving, the host processor 204 may go to sleep to achieve low power consumption. Suitable interrupt rules may be programmed to the range sensor 202 for the sensor to wake up the host processor 204 when a user approach is detected. When the user is not present, the host processor 204 may go to sleep. Afterwards, upon the human user arrival, the range sensor 202 runs the multiple threshold checkers to determine whether certain criteria are satisfied. In response to the satisfaction of the certain criteria, the range sensor 202 may send an interrupt to wake up the host processor 204, and the range sensor 202 may provide new measurement data as a result. The host processor 204 retrieves new measurement data. The host processor 204 runs breathing detection operations to detect the breathing pattern of the human user. In some embodiments, breathing detection operations may be performed after a certain time (e.g., a predetermined time) if no big motion is detected to confirm that the scene change that wakes up the host processor is coming from a human user that has approached the sensor (and then stopped moving), and not due to an object being pushed towards the sensor (and left stationary). The host processor 204 may then update the presence state machine. As part of updating the presence state machine, the host processor 204 may program specific sensor settings (e.g., updating settings of the multiple threshold checkers). In some embodiments, the checker settings may be programmed when the human user absence has been detected. If the host processor 204 determines that the human user is present, the interaction between the range sensor 202 and the host processor 204 may continue as shown in FIG. 2A. If the host processor 204 determines that the human user is not present, the host processor may program new checkers settings to "freeze" the scene and go back to sleep.

Threshold checkers can be a technique for a host computing device to only get interrupts when certain criteria are met. The host computing device sets the criteria for the threshold checkers. Each individual threshold checker has a specific zone and data type for threshold checking. In some embodiments, a total of 64 threshold checkers may be available in either the range sensor with the 16-zone mode or the range sensor with 64-zone mode. For the range sensor with the 16-zone mode, up to 4 range checkers per zone could be used. In some embodiments, all 64 threshold checkers could be implemented for an individual zone. If multiple checkers are used per zone, each of these multiple checkers can be OR'ed or AND'ed with the check output of the previous threshold checker.

Two special features may be added for each checker. The first feature is the "No Target" flag. With this flag set for a zone, an interrupt could be raised if no target is detected in the zone (e.g., as shown in the zone 102 in FIG. 1A). The second feature is the "AND/OR" flag, which indicates taking the current checker output, and either AND or OR the results with the previous checker results of the same zone.

FIG. 3 shows a range sensor checker's truth table, according to some embodiments. "Target found" means one target has been found with its target_status in the valid_target_status list. "No target found" means no target with its target_status in the valid_target_status list has been found. "Target found/No target found" does not apply to "per zone" based checkers. A range sensor may be able to detect more than 1 target per zone (typically 4 targets). Among those possible multiple targets, only one may be used for the checkers feature. Data types measured by the range sensor can be related to either a target or a zone. For instance, the distance or the signal rate are associated with a target, the ambient rate is related to a zone (not a target). Whatever the data type, the same low, high checker rules can be applied. Details of the fields in the range sensor truth table are explained below.

TABLE 1

| Parameter Name | Size (Bits) | Definition |
| --- | --- | --- |
| checker_param_low_thresh | 32 | see the data type to fill in these values which must match the checker_param_type<br>Example: For Median_Range_MM, this is a distance in mm |

TABLE 1-continued

| Parameter Name | Size (Bits) | Definition |
|---|---|---|
| checker_param_high_thresh | 32 | see the data type to fill in these values which must match the checker_param_type<br>Example: For Median_Range_MM, this is a distance in mm |
| checker_param_type | 8 | See Checker Parameter Type List<br>Example:: MEDIAN_RANGE_MM, PEAK_RATE_KCPS_PER_SPAD |
| checker_type | 8 | See Checker Type List<br>Example: IN_WINDOW, OUT_OF_WINDOW" |
| zone_num | 8 | Bit 5:0—Zone Address from 0 to 63<br>Bit 6—Not Defined<br>Bit 7—Set to 1 for last zone to be done on the checker list<br>Example: 0x0F is Zone 15, and this is not the last checker<br>0x8F is Zone 15 and this is the last checker |
| optional_checker_type | 8 | Bit 0—Zone Check for No Target - Interrupt will be set if no target detected in zone.<br>Bit 1—AND/OR - (1 == AND)/(0 == OR).<br>Bit 2—Not Defined<br>Bit 3—Not Defined<br>Bit 4—Not Defined<br>Bit 5—Not Defined<br>Bit 6—Not Defined<br>Bit 7—Not Defined<br>Example: 0x00 is No Target Detect is turned off, and it is an OR Checker<br>0x3 is No Target Detect is turned on, and it is an AND Checker |

Table 1 shows the threshold checker input data parameters, according to some embodiments. The parameter "checker_param_low_thresh" indicates the low threshold value of the checker range. The parameter "checker_param_high_thresh" indicates the high threshold value of the checker range. The parameter "checker_param_type" indicates the type of data that the check would examine. Examples of the parameter "checker_param_type" include MEDIAN_RANGE_MM and PEAK_RATE_KCPS_PER_SPAD. Details of the parameter "checker_param_type" are described below. The parameter "checker_type" indicates how the measurement data is compared to the checker thresholds (represented by "checker_param_low_thresh" and "checker_param_high_thresh"). Examples of the parameter "checker_type" include "IN_WINDOW" and "OUT_OF_WINDOW." Details of the parameter "checker_type" are described below. The parameter "zone_num" indicates the zone number that the checker is associated with. The parameter "optional_checker_type" may indicate optional checker parameters that can be added to the threshold checker. The checker parameters "checker_param_low_thresh" and "checker_param_high_thresh" may each be represented by 32 bits, according to some embodiments. Each of the checker parameters "checker_param_type," "checker_type," "zone_num," and "optional_checker_type" may be represented by 8 bits, according to some embodiments.

TABLE 2

| Name | V | Format | Min Value | Max Value | Units | Resolution | Target Or Zone Based Checker |
|---|---|---|---|---|---|---|---|
| INVALID_CHECKER | 0 | None | None | None | None | None | None |
| MEDIAN_RANGE_MM | 1 | signed 14.2 | −8192.0 | 8191.0 | (mm) | 0.25 | Target |
| PEAK_RATE_KCPS_PER_SPAD | 2 | unsigned 19.11 | 0.0 | 524287.0 | kcps/SPAD | 0.0005 | Target |
| RATE_SIGMA_KCPS_PER_SPAD | 3 | unsigned 19.11 | 0.0 | 524287.0 | kcps/SPAD | 0.0005 | Target |
| RANGE_SIGMA_MM | 4 | unsigned 9.7 | 0.0 | 511.0 | mm | 0.0078 | Target |
| TARGET_REFLECTANCE_EST | 5 | unsigned 7.1 | 0 | 127.0 | % | 0.5 | Target |
| MIN_RANGE | 6 | signed 14.2 | −8192.0 | 8192.0 | mm | 0.25 | Target |
| MAX_RANGE | 7 | signed 14.2 | −8192.0 | 8192.0 | mm | 0.25 | Target |
| AMB_RATE_KCPS_PER_SPAD | 8 | unsigned 12.7 | 0.0 | 4095 | kcps/SPAD | 0.0078 | Zone |
| NUM_OF_TARGETS | 9 | unsigned 8.0 | 0 | 4 | None | 1 | Zone |
| DMAX_MM | 10 | unsigned 14.0 | 0 | 16383 | mm | 1 | Zone |

TABLE 2-continued

| Name | V | Format | Min Value | Max Value | Units | Resolution | Target Or Zone Based Checker |
|---|---|---|---|---|---|---|---|
| SENSOR_TEMP | 11 | signed 8.0 | −40 | 125 | degree C. | 1 | Zone |
| SENSOR_TARGET_STATUS | 12 | unsigned 8.0 | 0 | 20 | None | 1 | Target |
| EFFECTIVE_SPAD_COUNT | 13 | unsigned 12.8 | 0 | 4095 | SPAD's | 0.0039 | Zone |
| DELTA_START_END_TEMP | 14 | unsigned 8.0 | 0 | 100 | None | 1 | Zone |
| DELTA_START_END_PHASE | 15 | | | | None | | Zone |

Table 2 shows the details of the checker parameter types corresponding to the parameter "checker_param_type" shown in Table 1, according to some embodiments. For each checker parameter type, the corresponding value, format, minimum value, maximum value, units, resolution, and whether the type is for a target based checker or a zone based checker may be defined.

In some embodiments, the value of 0 represents an invalid threshold checker. The value of 1 represents a type of the median range in mm ("MEDIAN_RANGE_MM"). The value of 2 represents a peak rate in kcps/SPAD ("PEAK_RATE_KCPS_PER_SPAD"). The value of 3 represents a sum rate in kcps/SPAD ("RATE_SIGMA_KCPS_PER_SPAD"). The value of 4 represents a sum range in mm ("RANGE_SIGMA_MM"). The value of 5 represents an estimated target reflectance percentage ("TARGET_REFLECTANCE_EST"). The value of 6 represents a minimum range in mm ("MIN_RANGE"). The value of 7 represents a maximum range in mm ("MAX_RANGE"). The value of 8 represents an ambient rate in kcps/SPAD ("AMB_RATE_KCPS_PER_SPAD"). The value of 9 represents the number of targets detected ("NUM_OF_TARGETS"). The value of 10 represents the maximum distance in mm ("DMAX_MM"). The value of 11 represents the temperature ("SENSOR_TEMP"). The value of 12 represents the target status ("SENSOR_TARGET_STATUS"). The value of 13 represents the effective SPAD (single-photon avalanche diode) count ("EFFECTIVE_SPAD_COUNT"). The value of 14 represents a change in temperature between the start and the end of a ranging period ("DELTA_START_END_TEMP"). The value of 15 represents a change in phase between the start and the end of a ranging period ("DELTA_START_END_PHASE").

Table 3 shows the details of the checker type corresponding to the parameter "checker_type" in Table 1, according to some embodiments. In some embodiments, the value of 0 represents the "IN_WINDOW" condition that, when the value is between the defined range (("checker_param_low_thresh"<=value) AND (value<="checker_param_high_thresh")), the interrupt generation condition for the threshold checker is satisfied. The value of 1 represents the "OUT_OF_WINDOW" condition that, when the value is outside the defined range (("checker_param_low_thresh">value) OR (value>"checker_param_high_thresh")), the interrupt generation condition for the threshold checker is satisfied. The value of 2 represents the "LESS_THAN_EQUAL_MIN_CHECKER" condition that, when the value is less than the minimum threshold of the range (value<"checker_param_low_thresh"), the interrupt generation condition for the threshold checker is satisfied. The value of 3 represents the "GREATER_THAN_MAX_CHECKER" condition that, when the value is greater than the maximum threshold of the range (value>"checker_param_high_thresh"), the interrupt generation condition for the threshold checker is satisfied. The value of 4 represents the "EQUAL_MIN_CHECKER" condition that, when the value is equal to the minimum threshold of the range (value="checker_param_low_thresh"), the interrupt generation condition for the threshold checker is satisfied. The value of 5 represents the "NOT_EQUAL_MIN_CHECKER" condition that, when the value is not equal to the minimum threshold of the range (value !="checker_param_low_thresh"), the interrupt generation condition for the threshold checker is satisfied. When there are multiple threshold checkers, the interrupt generation conditions for all the checkers may be combined (AND'ed or OR'ed) to determine whether an interrupt would be generated to wake up the host processor of the host computing device.

TABLE 3

| Name | Value | Definition of when Interrupt Generated |
|---|---|---|
| IN_WINDOW | 0 | (Min Threshold <= Value) AND (Value <= Max Threshold) |
| OUT_OF_WINDOW | 1 | (Min Threshold > Value) OR (Value > Max Threshold) |
| LESS_THAN_EQUAL_MIN_CHECKER | 2 | Value < Min Threshold |
| GREATER_THAN_MAX_CHECKER | 3 | Value > Max Threshold |
| EQUAL_MIN_CHECKER | 4 | Value = Min Threshold |
| NOT_EQUAL_MIN_CHECKER | 5 | Value != Min Threshold |

TABLE 4

| Name | Bit | Definition |
|---|---|---|
| Zone Number | 0:5 | Zone Value from o to 63 |
| N/A | 6 | Not Used |
| Last Zone | 7 | When this bit is set, this will be the last checker used to analyze for an interrupt condition |

Table 4 shows the details of the zone number corresponding to the parameter "zone_num" in Table 1, according to some embodiments. An 8-bit register per checker may be used to represent the zone number associated with a threshold checker. For the first 6 bits (bits 0:5) may be used to represent 64 zones. More bit(s) may be used if there are more than 64 zones. The last bit (bit 7) of the 8-bit register may be used to indicate whether the checker is associated with the last zone. When the last bit is set, the last bit indicates that the associated checker is the last checker of the last zone used to analyze the interrupt condition.

TABLE 5

| Name | Bit | Definition |
|---|---|---|
| No Target Detect | 0 | When this bit is set, if the checker is a target based (not Zone) checker, an interrupt will be generated if No Target is seen in this zone. |
| AND/OR | 1 | AND = 1, OR = 0: This bit lets the checker tests do a mathematical AND or OR with the previous checker results for a particular zone.<br>Note: For the first checker on each zone, this value must be a 0 (OR), as the default value for an interrupt is 0 (0 & 1 = 0). These checkers are run in order from checker 0 to 63<br>Example:<br>Checker 0 is on zone 0, Set for OR<br>Checker 1 is on zone 0 , Set for OR<br>Checker 2 is on zone 0, Set for AND<br>The output of the interrupt on this zone is as follows:<br>(Check0 \| Check1) & Check2 |
| Not Defined | 2:7 | Not Defined |

Table 5 shows the details of the optional checker parameters corresponding to the parameter "optional_checker_type" in Table 1, according to some embodiments. An 8-bit register per checker may be used to represent the optional checker parameters associated with a threshold checker. The first bit (bit 0) represents the "No Target" flag. When this bit is set, an interrupt generation condition is met if no target is detected in the corresponding zone and if the checker is a target based checker.

The second bit (bit 1) represents the "AND/OR" flag. This bit instructs the checker to test by performing a mathematical AND or OR with the previous checker results for a particular zone. For the first checker associated with each zone, this value is set to be 0 (OR), because the default value for an interrupt is no interrupt 0 (0 & 1=0). These checkers may be run in order from checker 0 to checker 63.

In one illustrative example shown in Table 5, a zone (zone 0) is associated with three threshold checkers (checkers 0-2). Bit 1 of the checker 0's optional checker parameter register is 0 (OR). Bit 1 of the checker 1's optional checker parameter register is 0 (OR). Bit 1 of the checker 2'S optional checker parameter register is 1 (AND). That means, the output of the interrupt generation from this zone 0 is ((checker 0 result) OR (checker 1 result)) AND (checker 2 result).

FIG. 4A shows an example of checker configurations for one zone, according to some embodiments. As shown in FIG. 4A, 5 threshold checkers (checkers 0-4) are configured. Checkers 0, 2, and 3 are associated with the zone 0. Checkers 1 and 4 are associated with the zone 1.

Checker o's parameter type is the median range in mm ("MEDIAN_RANGE_MM"). The configured range for checker 0 is from 1050 mm to 1550 mm. The checker type for checker 0 is "IN_WINDOW." That means, if the detected median range is between 1050 mm and 1550 mm, the result of checker 0 is TRUE. The "No target detected" flag for checker 0 is set. So, if there is no target detected in the zone 0, the result of checker 0 is also TRUE. Because checker 0 is the first checker of the zone 0, the "AND/OR" flag of checker 0 is "OR."

Checker 2'S parameter type is the peak rate in kcps/SPAD ("PEAK_RATE_KCPS_PER_SPAD"). The configured range for checker 2 is from 50.0 kcps/SPAD to 500 kcps/SPAD. The checker type for checker 2 is "IN_WINDOW." That means, if the detected peak rate is between 50.0 kcps/SPAD and 500 kcps/SPAD, the result of checker 2 is TRUE. The "AND/OR" flag of checker 2 is "AND."

Checker 3's parameter type is the temperature ("SENSOR_TEMP"). The configured high threshold for checker 3 is −20° C., and the low threshold is not applicable. The checker type for checker 3 is "GREATER_THAN_MAX_CHECKER." That means, if the detected temperature is above −20° C., the result of checker 3 is TRUE. The "AND/OR" flag of checker 3 is "AND."

Combining the results of the 3 checkers for the zone 0 based on the "AND/OR" flag settings for checker 0 (OR), checker 2 (AND), and checker 3 (AND), the combined result for the zone 0 threshold checkers would be (checker 0 result) AND (checker 2 result) AND (checker 3 result).

For the zone 1, checker 1's parameter type is the median range in mm ("MEDIAN_RANGE_MM"). The configured low threshold is 350 mm. The high threshold is not applicable for checker 1. The checker type for checker 1 is "LESS_THAN_EQUAL_MIN_CHECKER." That means, if the detected median range is less than 350 mm, the result of checker 1 is TRUE. Because checker 1 is the first checker of the zone 1, the "AND/OR" flag of checker 1 is "OR."

Checker 4's parameter type is the ambient rate in kcps/SPAD ("AMB_RATE_KCPS_PER_SPAD"). The configured low threshold for checker 4 is 50 kcps/SPAD. The checker type for checker 4 is "LESS_THAN_EQUAL_MIN_CHECKER." That means, if the detected ambient rate is below so kcps/SPAD, the result of checker 4 is TRUE. The "AND/OR" flag of checker 4 is "AND."

Combining the results of the 2 checkers for the zone 1 based on the "AND/OR" flag settings for checker 1 (OR) and checker 4 (AND), the combined result for the zone 1 checkers would be (checker 1 result) AND (checker 4 result).

FIG. 4B shows the example checker configurations for 5 checkers, according to some embodiments. The checker configurations for checkers 0-4 are the same as the corresponding checker configurations in FIG. 4A, except that the same configurations are shown in the hexadecimal and decimal formats in FIG. 4B.

FIG. 5A shows the example application programming interface (API) definitions, according to some embodiments. The API sttof_al_set_ic_global_cfg is used to set the interrupt control global configuration and the valid target status list configuration. The API sttof_al_set_ic_checkers is used to set the threshold checkers on the range sensor. The API sttof_al_get_ic_op_status is used to get the interrupt status for each zone.

FIG. 5B shows the example code to configure the global configuration and the valid target status list, according to some embodiments. The example code in FIG. 5B may use the API sttof_al_set_ic_global_cfg as defined with respect to FIG. 5A.

FIG. 5C shows the example code to configure 16 threshold checkers, according to some embodiments. The example code in FIG. 5C may use the API sttof_al_set_ic_checkers as defined with respect to FIG. 5A.

The disclosed embodiment techniques allow a sensor (e.g., a range sensor) to pre-process many zones of raw data that meet certain criteria deemed as an event for an application running on the host computing device. The criteria for a checker can be changed from event to event, as the criteria of one event may be completely different than the criteria needed for the next event. For example, in the event of a human user departure being detected, the criteria settings for a checker may change.

The host processor only needs to be woken up when an event occurred. The host processor could determine the criteria for the next event, update the settings for the threshold checkers inside the sensor to meet such criteria, and then go to sleep. Once the new criteria is met, the host processor is again woken up to process the updated data, and the host processor is be able to go back to sleep.

The disclosed multiple threshold checker techniques allow multiple checker parameters to meet specific criteria and allow different threshold checkers per zone. The results of multiple checkers can be combined using AND or OR operations. The disclosed checker techniques lower the overall power consumption and reduces processing time for the host processor because transfer of massive amount of measurement data from the sensor for the host computing device to further process is not necessary.

Figure 6:
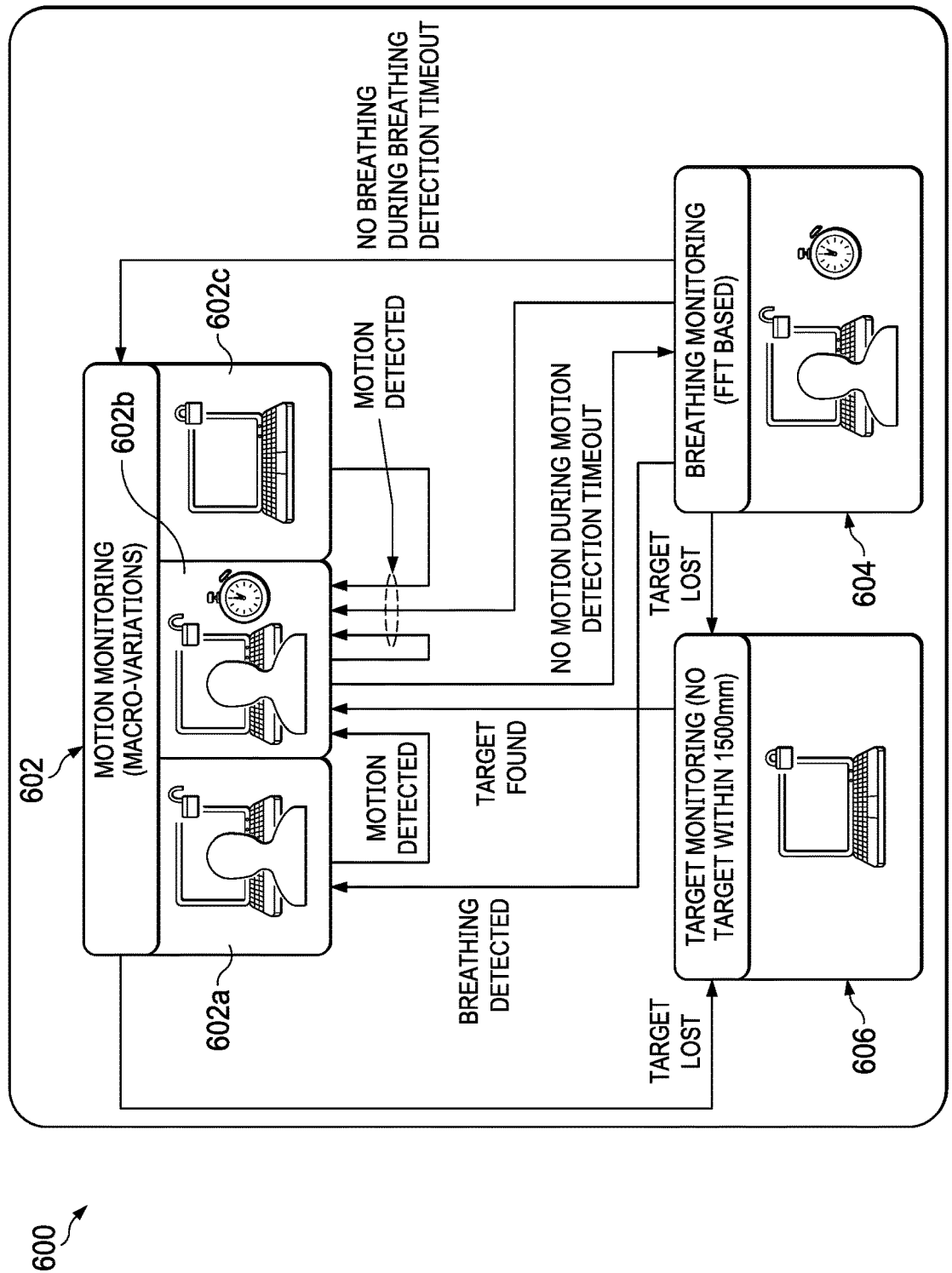
FIG. 6 illustrates a presence state machine used by a presence detection application, according to some embodiments.

With the context of presence detection, another technical challenge of using a low resolution sensor (e.g., a range sensor) is to accurately detect the presence of a human user (e.g., distinguishing the breathing of the human user from detection of a static object, such as a chair). FIG. 6 illustrates a presence state machine 600 used by a presence detection application, according to some embodiments. The presence state machine 600 includes three states, the motion monitoring state 602, the breathing monitoring state 604, and the target monitoring state 606. The motion monitoring state 602 may have 3 macro variations 602a, 602b, and 602c. The presence detection application may analyze the measurement data provided by the range sensor to determine an input to the current state of the presence state machine 600, such as "motion detected," "breathing detected," "no breathing," "no motion," "target found," and "target lost." Based on the input and the current state, the presence detection application may determine whether and how the current state of the presence state machine 600 is transitioned to a different state. The arrows in FIG. 6 indicate the directions of state transitions from one state to another state.

For example, if the current state of the presence state machine 600 is the breathing monitoring state 604, and the presence detection application determines that "target lost" is detected, the current state of the presence state machine 600 may transition to the target monitoring state 606. If the current state of the presence state machine 600 is the breathing monitoring state 604, and the presence detection application determines that breathing is detected, the current state of the presence state machine 600 may transition to the variation 602a of the motion monitoring state 602. If the current state of the presence state machine 600 is the breathing monitoring state 604, and the presence detection application determines that "no breathing" is detected during a breathing detection timeout period, the current state of the presence state machine 600 may transition to the variation 602c of the motion monitoring state 602.

To further improve accuracy of presence detection, embodiments of this disclosure provide fast Fourier transform (FFT) based techniques to help detect breathing movement of a human user.

As described above, threshold checker techniques may be used to filter out noise from human motion before the sensor measured data is transferred to the presence detection application running on the host computing device. For example, in the breathing monitoring state 604, the presence detection application may program the range sensor with specific settings for the checkers in terms of the resolution, power consumption, ranging frequency, and measurement accuracy.

The embodiment FFT based breathing detection techniques may be applied in conjunction with or independent of threshold checker techniques described above. In any event, an FFT can be performed on the measurement data of the sensor to generated transformed measurement data in the frequency domain. The transformed measurement data in the frequency domain is then analyzed to identify a peak corresponding to breathing. The embodiment FFT based breathing detection techniques further help remove the measurement noise and help identify movement of a human user's breathing. The FFT based breathing detection techniques are described as part of the presence detection application running on the host computing device, according to some embodiments. But, this is purely for illustration purpose. The FFT based breathing detection techniques described in this disclosure may also run on the sensor in other embodiments.

FIG. 7A shows the example signal patterns in the situation of human user breathing. The graph 702 depicts the distance measurement data over time in the time domain. The graph 704 depicts the corresponding transformed measurement data in the frequency domain. As shown in FIG. 7A, a breathing-coherent peak 706 in the frequency domain is detected. Accordingly, the breathing detection result 708 is TRUE ("breathing detected").

FIG. 7B shows the example signal patterns in the situation of a static chair. The graph 712 depicts the distance measurement data over time in the time domain. The graph 714 depicts the corresponding transformed measurement data in the frequency domain. As shown in FIG. 7B, no peak in the frequency domain indicates that there is no breathing. Accordingly, the breathing detection result 718 is FALSE ("no breathing detected").

For certain types of processors, the FFT operations may be heavy operations. For processors with limited processing power, the FFT operations may be performed only for some zones of interest and at the right time. The embodiment FFT based breathing detection techniques may be adaptive to the ranging frequencies of specific sensors. In some embodiments, the ranging frequency may be increased to have a wider frequency domain spectrum for analyzing faster motions and accurately providing the breathing frequency of the human user.

Figure 8:
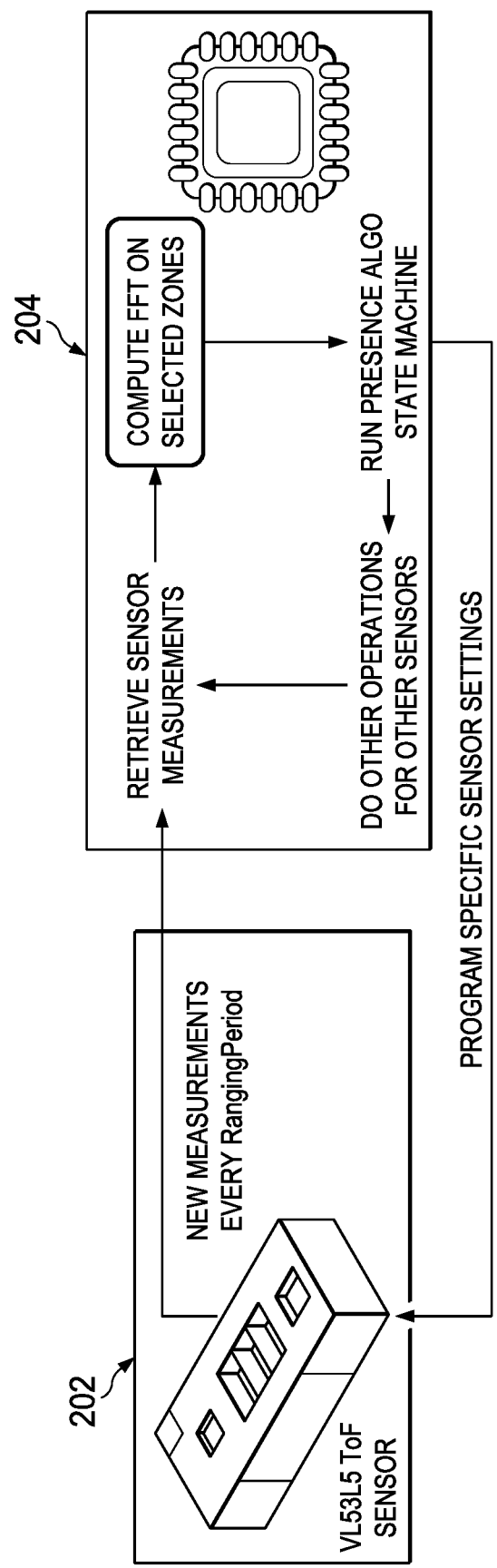
FIG. 8 illustrates the interaction between a range sensor and a host processor incorporating the FFT based breathing detection techniques, according to some embodiments.

FIG. 8 illustrates the interaction between a range sensor 202 and a host processor 204 incorporating the FFT based breathing detection techniques, according to some embodiments. The range sensor 202 is continuously monitoring the scene and sends out the measurement data to the host processor 204 for analysis. The range sensor 202 provides new measurement data for every ranging period, which is retrieved by the host processor 204. The host processor 204 may compute FFT on the retrieved sensor measurement data for breathing detection. The FFT operations may be performed only on selected zones. In some embodiments, the zones for FFT may be selected based on valid distance output being below a certain distance threshold. Because the valid distance outputs may change from iteration to iteration, for every iteration, new zones may be designated for FFT operations when the range sensor provides new measurement data for the next ranging period. The host processor 204 may then update the presence state machine. A new event may be triggered as the presence state machine is updated. As part of updating the presence state machine, the host processor 204 may program specific sensor settings (e.g., updating settings of the multiple threshold checkers). The updated settings may be based on the triggered next event. The host processor 204 may also perform other operations for other sensors, and continue to retrieve new measurement data from the range sensor 202 for the next ranging period.

Figure 9:
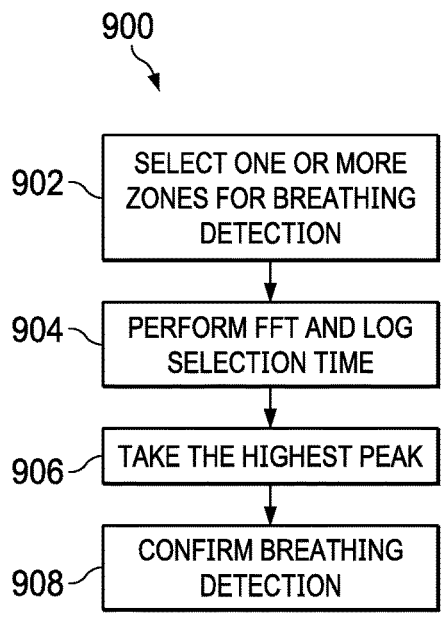
FIG. 9 illustrates a flowchart of a method 900 for detecting a human user by examining a breathing peak in the frequency domain, according to some embodiments.

FIG. 9 illustrates a flowchart of a method 900 for detecting a human user by examining a breathing peak in the frequency domain, according to some embodiments. The method 900 may be carried out or performed by routines, subroutines, or modules of software executed by one or more processors of a computing device, such as the host processor of a host computing device. Purely for the purpose of illustration, the method 900 is described as the method is performed by a presence detection application on the host computing device. The method 900 may also be carried out or performed by routines, subroutines, or modules of software executed by a sensor described in this disclosure. Coding of the software for carrying out or performing the method 900 is well within the scope of a person of ordinary skill in the art having regard to the present disclosure. The method 900 may include additional or fewer operations than those shown and described and may be carried out or performed in a different order. Computer-readable code or instructions of the software executable by the one or more processor of the computing device may be stored on a non-transitory computer-readable medium, such as for example, memory of the computing device and the sensor. The method 900 may also be implemented using hardware technologies such as ASIC (application-specific integrated circuit) or FPGA (field-programmable gate array) on a sensor or on a host computing device (e.g., as part of the presence detection application).

The method 900 starts at the operation 902, where the presence detection application selects one or more zones for breathing detection. Zone selection may be based on several conditions. Zone selection may be based on whether the selected zone has at least one target. Zones with reported target status among 5, 6, and 9 (valid targets) may be selected. In a case of several targets having valid status, the zone with the highest peak rate may be selected. Zone selection may also be based on whether the reported distance is below a zone selection distance threshold. In one embodiment, the zone selection distance threshold is 1500 mm. These conditions may need to be held for a zone selection period (e.g., 10 seconds) for the zone to qualify for zone selection.

At the operation 904, during the microcontroller (MCU) loop, and at the FFT computation phase, the presence detection application may perform the FFT on one selected zone and log execution time. Since the ranging period is known, the presence detection application can estimate how many FFTs can then be computed until the next ranging period from the range sensor. This would intrinsically take into account the MCU workload at that time.

In some embodiments, one principle for the described FFT based techniques is not to compute the FFT for a zone at a second time if all selected zones do not have one FFT computation for at least once. In that way, FFT may be performed sequentially and with whatever ranging period as needed. Indeed, different ranging periods may be needed for detecting different user behavior.

At the operation 906, once the FFT is performed, the presence detection application may take the highest peak in the frequency domain. In some embodiments, in order to be qualified as a possible breathing detection, this highest peak may need to have amplitude between two threshold values and located between two frequencies, and the amplitude may need to be higher than a certain number of times of the mean of the entire frequency domain spectrum of the measurement data. The parameters indicated alongside may be tunable to detect different human user behavior.

At the operation 908, the state machine for the presence detection application confirms the breathing detection. For the state machine to consider a zone with confirmed breathing, the breathing may need to be persistent for at least a breathing detection period. In one embodiment, breathing detection period is 4 seconds.

In the context of presence detection for host computing devices (e.g., laptops), time of flight (ToF) sensors could be used because these sensors are low in power and are trustworthy in terms of privacy. Contrary to high resolution image sensors (e.g., cameras), it is not possible from the low resolution range sensor output to tell what is happening in front of the laptop, but only whether there is someone or not.

Processing the sensor measurement data is technically challenging. The described embodiment techniques provide technical solutions to accurately determine the human presence in front of the sensor while improving the processing time of the host processor and reducing the overall power consumption.

Figure 10:
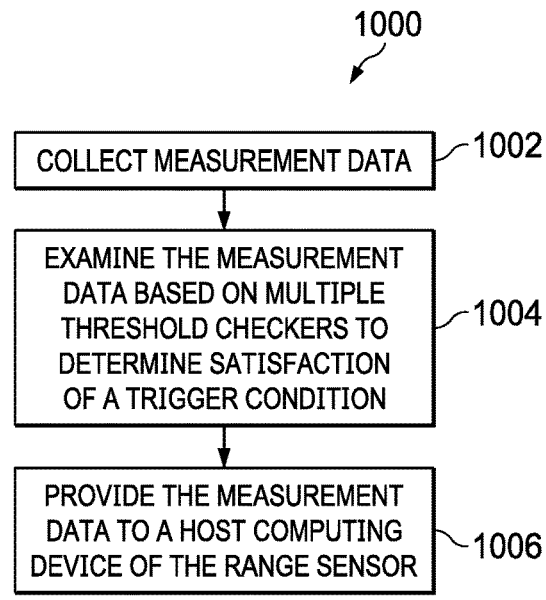
FIG. 10 illustrates a flowchart of a method 1000 for utilizing multiple threshold checkers, according to some embodiments.

FIG. 10 illustrates a flowchart of a method 1000 for utilizing multiple threshold checkers, according to some embodiments. The method 1000 may be carried out or performed by routines, subroutines, or modules of software executed by a sensor, such as a ToF range sensor, as described in this disclosure. Coding of the software for carrying out or performing the method woo is well within the scope of a person of ordinary skill in the art having regard to the present disclosure. The method 1000 may include additional or fewer operations than those shown and described and may be carried out or performed in a different order. Computer-readable code or instructions of the software executable by the one or more processor of the computing device may be stored on a non-transitory computer-readable medium, such as for example, memory of the sensor. The method woo may also be implemented using hardware technologies such as ASIC (application-specific integrated circuit) or FPGA (field-programmable gate array) on a sensor.

The method 1000 starts at the operation 1002, where the range sensor collects measurement data. At the operation 1004, the range sensor examines the measurement data based on multiple threshold checkers to determine satisfaction of a trigger condition. At the operation 1006, in response to the satisfaction of the trigger condition, the range sensor provides the measurement data to a host computing device of the range sensor.

In some embodiments, to provide the measurement data to the host computing device, the range sensor may generate an interrupt signal to wake up the host computing device. The range sensor may receive, from the host computing device, a measurement data request. The range sensor may then send, to the host computing device, a measurement data response including the measure data.

In some embodiments, the multiple threshold checkers may comprise a first threshold checker and a second threshold checker. The first threshold checker may include a first data type and a first threshold range. The second threshold checker may include a second data type and a second threshold range. The first data type may be different from the second data type.

In some embodiments, the first data type may be one of a signal rate type, a reflectance type, a distance type, or an ambient rate type.

In some embodiments, the multiple threshold checkers may comprise a first subset of threshold checkers associated with a first zone measured by the range sensor. The multiple threshold checkers may further comprise a second subset of threshold checkers associated with a second zone measured by the range sensor.

In some embodiments, one device of the range sensor or the host computing device may perform breathing analysis operations using the measurement data. To perform the breathing analysis operations, the one device may perform fast Fourier transform (FFT) on the measurement data to generate transformed measurement data in the frequency domain. The one device may identify a highest peak in the transformed measurement data corresponding to breathing detection. The one device may confirm the breathing detection based on the identifying the highest peak.

In some embodiment, to identify the highest peak, the one device may determine that the amplitude of the highest peak is between a first amplitude threshold and a second amplitude threshold and that the amplitude is higher than N times of a mean of the transformed measurement data. N may be an integer great than or equal to 2.

In some embodiments, the measurement data may comprise first measurement data associated with a first zone and second measurement data associated with a second zone. To perform the FFT on the measurement data, the one device may determine that a first distance of the first measurement data is less than a zone selection distance threshold. The one device may determine that a second distance of the second measurement data is greater than the zone selection distance threshold. The one device may perform the FFT on the first measurement data without performing the FFT on the second measurement data.

In some embodiments, the range sensor may receive updated settings for at least one of the multiple threshold checkers. The updated settings may be based on a next event associated with a presence state machine running on the host computing device. The next event may be triggered by the providing the measurement data to the host computing device. The range sensor may examine the measurement data based on the multiple threshold checkers including the at least one threshold checker with the updated settings.

Figure 11:
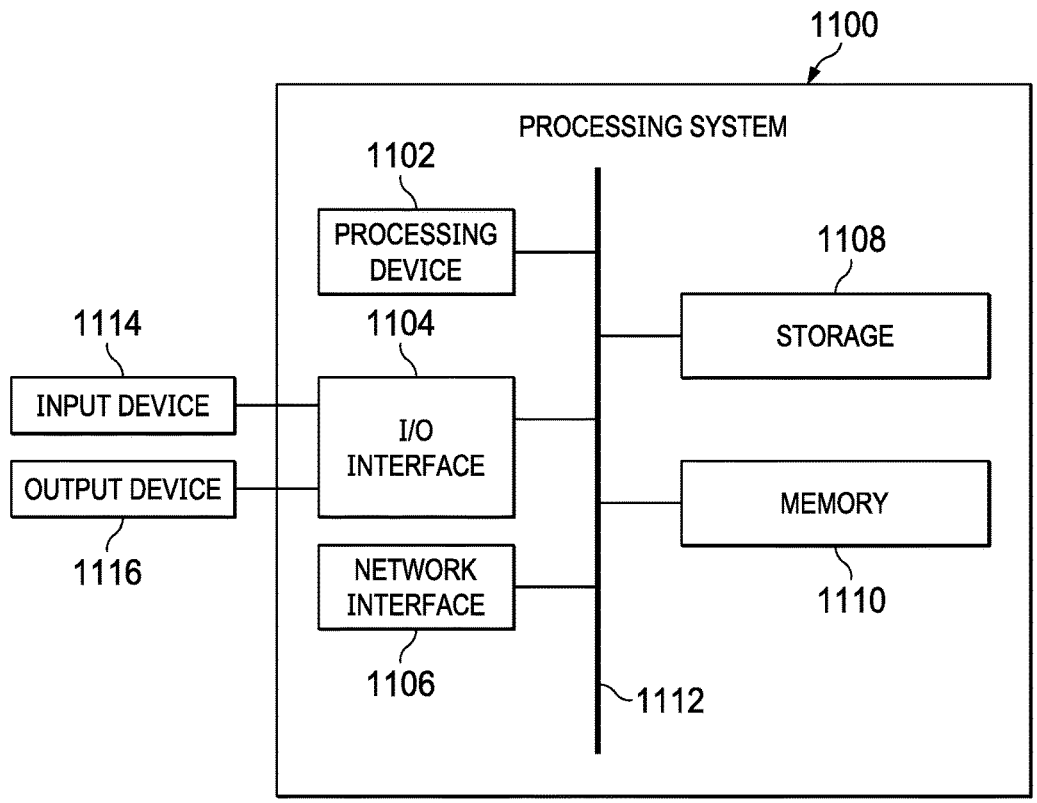
FIG. 11 is a block diagram of an example processing system used to implement the disclosed embodiments.

FIG. 11 is a block diagram of an example processing system 1100, which may be used to implement embodiments disclosed herein, and provides a higher level implementation example. The computing device may be the host computing device described herewith. The computing device as described above may be implemented using the example processing system 1100, or variations of the processing system 1100. Specific devices may utilize all of the components shown, or only a subset of the components and levels of integration may vary from device to device. The processing system 1100 could be a smart phone, a server, a desktop terminal, for example, or any suitable processing system. Other processing systems suitable for implementing embodiments described in the present disclosure may be used, which may include components different from those discussed below. Although FIG. 11 shows a single instance of each component, there may be multiple instances of each component in the processing system 1100.

The processing system 1100 may include one or more processors 1102, such as a processor, graphics processing unit (GPU), a microprocessor, an application-specific integrated circuit (ASIC), a field-programmable gate array (FPGA), a dedicated logic circuitry, a tensor processing units (TPU), an artificial intelligence (AI) accelerator, or combinations thereof. The processing system 1100 may also include one or more input/output (I/O) interfaces 1104, which may enable interfacing with one or more appropriate input devices 1114 and/or output devices 1116. The processing system 1100 may include one or more network interfaces 1106 for wired or wireless communication with a network (e.g., an intranet, the Internet, a P2P network, a WAN and/or a LAN) or other node. The network interfaces 1106 may include wired links (e.g., Ethernet cable) and/or wireless links (e.g., one or more antennas) for intra-network and/or inter-network communications.

The processing system 1100 may also include one or more storage units 1108, which may include a mass storage unit such as a solid state drive, a hard disk drive, a magnetic disk drive and/or an optical disk drive. The processing system 1100 may include one or more memories 1110, which may include a volatile or non-volatile memory (e.g., a flash memory, a random access memory (RAM), and/or a read-only memory (ROM)). The non-transitory memory(ies) 1110 may store instructions for execution by the one or more processors 02, such as to carry out examples described in the present disclosure. The one or more memories 1110 may include other software instructions, such as for implementing an operating system and other applications/functions. In some examples, one or more data sets and/or modules may be provided by an external memory (e.g., an external drive in wired or wireless communication with the processing system 1100) or may be provided by a transitory or non-transitory computer-readable medium. Examples of non-transitory computer readable media include a RAM, a ROM, an erasable programmable ROM (EPROM), an electrically erasable programmable ROM (EEPROM), a flash memory, a CD-ROM, or other portable memory storage. There may be a bus 1112 providing communication among components of the processing system 1100, including the one or more processors 1102, I/O interface(s) 1104, network interface(s) 1106, storage unit(s) 1108, and the one or more memories 1110. The bus 1112 may be any suitable bus architecture including, for example, a memory bus, a peripheral bus or a video bus.

The processing system 1100 may also include one or more sensors (not shown). Examples of sensors hosted by the processing system 1100 may include a range sensor (e.g., a ToF range sensor) and a high resolution camera sensor. In some embodiments, the range sensor and the high resolution camera sensor may be internal devices of the processing system 1100. In other embodiments, the range sensor and the high resolution camera sensor may be external devices connected to the processing system 1100 through the I/O interface(s) 1104.

In FIG. 1*i*, the input device(s) 1114 (e.g., a keyboard, a mouse, one or more microphones, a touchscreen, and/or a keypad) and output device(s) 1116 (e.g., a display, a speaker and/or a printer) are shown as external to the processing system 1100. In other examples, one or more of the input device(s) 1114 and/or the output device(s) 1116 may be included as a component of the processing system 1100. In other examples, there may not be any input device(s) 1114 and output device(s) 1116, in which case the I/O interface(s) 1104 may not be needed.

While this disclosure has been described with reference to illustrative embodiments, this description is not intended to be construed in a limiting sense. Various modifications and combinations of the illustrative embodiments, as well as other embodiments of the disclosure, will be apparent to persons skilled in the art upon reference to the description. It is therefore intended that the appended claims encompass any such modifications or embodiments.

What is claimed is:

1. A method comprising:
   collecting, by a sensor, measurement data;
   examining, by the sensor, the measurement data based on multiple threshold checkers to determine satisfaction of a trigger condition,
   the multiple threshold checkers comprising a first threshold checker, a second threshold checker, a third threshold checker, and a fourth threshold checker, the first threshold checker including a first threshold data type of distance or distance range, the second threshold checker including a second threshold data type of signal rate, the third threshold checker including a third threshold data type of reflectance, the fourth threshold checker including a fourth threshold data type of ambient rate, the first threshold data type being different from the second threshold data type, wherein the signal rate is different from any threshold data type of distance and different from any threshold data type of distance range; and
   in response to the satisfaction of the trigger condition:
      generating, by the sensor, an interrupt signal to wake up a host device; and
      sending, by the sensor to the host device, the measurement data.

2. The method of claim 1, the sending comprising:
   receiving, by the sensor from the host device, a measurement data request; and
   sending, by the sensor to the host device, a measurement data response including the measurement data.

3. The method of claim 1, the multiple threshold checkers further comprising a fifth threshold checker including a second threshold range.

4. The method of claim 1, the multiple threshold checkers comprising a first subset of threshold checkers associated with a first zone measured by the sensor and a second subset of threshold checkers associated with a second zone measured by the sensor.

5. The method of claim 1, further comprising:
   performing breathing analysis operations for presence detection using the measurement data, the performing the breathing analysis operations comprising:
   performing fast Fourier transform (FFT) on the measurement data to generate transformed measurement data in a frequency domain; and
   identifying a highest peak in the transformed measurement data corresponding to breathing detection; and
   confirming the breathing detection based on the identifying the highest peak.

6. The method of claim 5, wherein the breathing analysis operations are performed by one of the host device or the sensor.

7. The method of claim 5, the identifying the highest peak comprising:
   determining that an amplitude of the highest peak is between a first amplitude threshold and a second amplitude threshold and that the amplitude is higher than N times of a mean of the transformed measurement data, N being an integer great than or equal to 2.

8. The method of claim 5, the measurement data comprising first measurement data associated with a first zone and second measurement data associated with a second zone, the performing the FFT on the measurement data comprising:
   determining that a first distance of the first measurement data is less than a zone selection distance threshold;
   determining that a second distance of the second measurement data is greater than the zone selection distance threshold; and
   performing the FFT on the first measurement data without performing the FFT on the second measurement data.

9. The method of claim 1, further comprising:
   receiving, by the sensor, updated settings for at least one threshold checker of the multiple threshold checkers, the updated settings based on a next event associated with a presence state machine running on the host device, the next event triggered by the sending the measurement data to the host device, wherein the examining comprises:
   examining, by the sensor, the measurement data based on the multiple threshold checkers including the at least one threshold checker with the updated settings.

10. A sensor apparatus comprising:
    a memory;
    one or more processors coupled to the memory, the one or more processors configured to perform operations, the operations comprising:
    collecting measurement data;
    examining the measurement data based on multiple threshold checkers to determine satisfaction of a trigger condition,
    the multiple threshold checkers comprising a first threshold checker, a second threshold checker, a third threshold checker, and a fourth threshold checker, the first threshold checker including a first threshold data type of distance or distance range, the second threshold checker including a second threshold data type of signal rate, the third threshold checker including a third threshold data type of reflectance, the fourth threshold checker including a fourth threshold data type of ambient rate, the first threshold data type being different from the second threshold data type, wherein the signal rate is different from any threshold data type of distance and different from any threshold data type of distance range; and
    in response to the satisfaction of the trigger condition:
       generating an interrupt signal to wake up a host device; and
       sending to the host device, the measurement data.

11. The sensor apparatus of claim 10, the sending comprising:
    receiving, from the host device, a measurement data request; and
    sending, to the host device, a measurement data response including the measurement data.

12. The sensor apparatus of claim 10, the multiple threshold checkers further comprising a fifth threshold checker including a second threshold range.

13. The sensor apparatus of claim 10, the multiple threshold checkers comprising a first subset of threshold checkers associated with a first zone measured by the sensor apparatus and a second subset of threshold checkers associated with a second zone measured by the sensor apparatus.

14. The sensor apparatus of claim 10, the operations further comprising:
performing breathing analysis operations for presence detection using the measurement data, the performing the breathing analysis operations comprising:
performing fast Fourier transform (FFT) on the measurement data to generate transformed measurement data in a frequency domain; and
identifying a highest peak in the transformed measurement data corresponding to breathing detection; and
confirming the breathing detection based on the identifying the highest peak.

15. The sensor apparatus of claim 14, the identifying the highest peak comprising:
determining that an amplitude of the highest peak is between a first amplitude threshold and a second amplitude threshold and that the amplitude is higher than N times of a mean of the transformed measurement data, N being an integer great than or equal to 2.

16. The sensor apparatus of claim 14, the measurement data comprising first measurement data associated with a first zone and second measurement data associated with a second zone, the performing the FFT on the measurement data comprising:
determining that a first distance of the first measurement data is less than a zone selection distance threshold;
determining that a second distance of the second measurement data is greater than the zone selection distance threshold; and
performing the FFT on the first measurement data without performing the FFT on the second measurement data.

17. The sensor apparatus of claim 10, the operations further comprising:
receiving updated settings for at least one threshold checker of the multiple threshold checkers, the updated settings based on a next event associated with a presence state machine running on the host device, the next event triggered by the sending the measurement data to the host device, wherein the examining comprises:
examining the measurement data based on the multiple threshold checkers including the at least one threshold checker with the updated settings.

18. A system comprising:
a host processor of a host device;
a sensor, the sensor configured to perform sensor operations, the sensor operations comprising:
collecting measurement data;
examining the measurement data based on multiple threshold checkers to determine satisfaction of a trigger condition,
the multiple threshold checkers comprising a first threshold checker, a second threshold checker, a third threshold checker, and a fourth threshold checker, the first threshold checker including a first threshold data type of distance or distance range, the second threshold checker including a second threshold data type of signal rate, the third threshold checker including a third threshold data type of reflectance, the fourth threshold checker including a fourth threshold data type of ambient rate, the first threshold data type being different from the second threshold data type, wherein the signal rate is different from any threshold data type of distance and different from any threshold data type of distance range; and
in response to the satisfaction of the trigger condition:
generating an interrupt signal to wake up the host device; and
sending, to the host device, the measurement data.

19. The system of claim 18, the sending comprising:
receiving, from the host device, a measurement data request; and
sending, to the host processor of the host device, a measurement data response including the measurement data.

20. The system of claim 18, wherein one of the sensor or the host processor is configured to perform breathing analysis operations using the measurement data by:
performing fast Fourier transform (FFT) on the measurement data to generate transformed measurement data in a frequency domain; and
identifying a highest peak in the transformed measurement data corresponding to breathing detection; and
confirming the breathing detection based on the identifying the highest peak.

* * * * *